United States Patent [19]
Blumenfeld

[11] Patent Number: 5,170,788
[45] Date of Patent: Dec. 15, 1992

[54] NEEDLE ELECTRODE AND METHOD OF ASSEMBLY THEREOF

[75] Inventor: Arthur Blumenfeld, Brewster, N.Y.

[73] Assignee: Vickers Plc, London, United Kingdom

[21] Appl. No.: 690,856

[22] Filed: Apr. 24, 1991

[51] Int. Cl.⁵ ........................................... A61B 5/0492
[52] U.S. Cl. .................................. 128/642; 128/784; 29/862; 29/863
[58] Field of Search ............... 128/642, 733, 741, 784; 606/862, 863; 163/1, 5

[56] References Cited

U.S. PATENT DOCUMENTS

| | | |
|---|---|---|
| 3,147,750 | 9/1964 | Fry ........................................ 128/642 |
| 3,698,394 | 10/1972 | Piper et al. ....................... 128/784 X |
| 4,034,762 | 7/1977 | Cosens et al. ..................... 606/50 X |
| 4,295,467 | 10/1981 | Mann et al. ............................ 606/44 |

FOREIGN PATENT DOCUMENTS 651428 10/1931 Fed. Rep. of Germany ........ 606/49

Primary Examiner—Lee S. Cohen
Attorney, Agent, or Firm—Charles E. Baxley

[57] ABSTRACT

An electrode has a ferrule, a cannula and a wire, each with a distal end and a proximal end. The ferrule has a nose portion at its distal end and defines a nose passage terminating at a shoulder communicating with a passage having a guide opening followed by an abutment and opening into an annular recess. The proximal cannula end penetrates the nose passage and abuts the shoulder. The nose portion connects to the proximal cannula end. An insulator spool has a distal end an an axial bore smaller than the guide opening. A connective member has a cavity receiving the proximal wire end and is attached about the cavity to the proximal wire end and is secured in the axial bore of the spool that is in the annular recess with the distal wire end penetrating through the axial bore, the guide opening, and an interior cannula passage with the distal end of the spool engaging the abutment. An assembly method involves connecting the ferrule nose portion about the proximal cannula end, attaching the connector member about the cavity onto the proximal wire end, mounting the connector member into the spool bore, and inserting the spool in the annular recess with the distal wire end penetrating the axial bore, the guide opening and the interior cannula passage with the distal spool end engages the abutment.

21 Claims, 2 Drawing Sheets

NEEDLE ELECTRODE AND METHOD OF ASSEMBLY THEREOF

BACKGROUND OF THE INVENTION

This invention relates to a needle electrode and to a method of assembly thereof.

Needle electrodes have become important in the medical field, for example, to enable the detection of electrical activity in muscle fibers. Such needle electrodes can be used in conjunction with neurophysical recording systems to record and thereby diagnose a wide range of muscular and neurological disorders, and are particularly useful if provided in disposable form and to this end are usually provided with a sheath which is removed before use. The used needle electrode is discarded.

A prior art method of making a needle electrode is described in some detail hereinafter. The prior art method entails some problems. One such problem is that the prior art method includes the step of threading or pushing a needle wire through a cannula, which is an inherently difficult and hence a lengthy, time-consuming and expensive operation. What is worse, when the needle wire has been provided with an insulating coating, this coating can be scraped off by the mere action of pushing the needle wire through the cannula, resulting in short-circuiting the needle electrode during its manufacture and rendering it scrap, unfit for use.

The present invention overcomes and avoids the foregoing problems of the prior art needle electrode, and also overcomes the problems of the prior art method of making the prior art needle electrode.

It is accordingly an important object of the present invention to provide a needle electrode of increased reliability relative to the prior art needle electrode.

It is another object of the invention to provide a needle electrode of decreased cost relative to the prior art needle electrode.

It is a further object of the invention to provide a method of making a needle electrode that is faster and less expensive than the prior art method.

It is an additional object of the invention to provide a method of making a needle electrode that is more reliable in use than the prior art needle electrode.

A patentability search on the disclosure of the present invention has identified the following U.S. Pat. Nos.:

4,317,458 Yokoyama
4,408,610 Sarnoff
4,805,625 Wyler
4,892,625 Prass

The search was extended to cover foreign art without uncovering any foreign references more pertinent than the above-identified U.S. patents.

Yokoyama addresses an electrode apparatus for cardiac pacing suitable for use in emergency circumstances. Sarnoff also presents an electrode suitable for emergency circumstances. Ritter teaches electrodes which are particularly useful as temporary heart pacer electrodes for cardiac stimulation during and after surgical procedures. Wyler introduces a sphenoidal electrode and insertion method. Prass envisages a handheld instrument for electrically stimulating exposed, subcutaneous tissue of a living body.

Further comments on the above-identified prior art patents follow;

Yokoyama and Wyler are concerned with surgical techniques involving the insertion of a needle and a sheath into tissue and withdrawing the sheath after the needle has become embedded in the tissue. There is relative movement of the sheath and the needle but the relative movement occurs only during use of the device.

Sarnoff discloses a conventional hypodermic needle arranged within a closed housing to maintain the needle sterile.

Ritter is concerned with a design of needle and pin which can be easily separated by being pulled apart.

Prass is not really concerned with a needle, but rather with a probe with a planar tip to facilitate making electrical contact. Moreover, the method of construction involves the use of a heat-shrinkable sleeve 54 around portions of a tube 50 and a male connector 40.

These references bear little or no significance to the present invention and do not anticipate the present invention in either its article aspect or its method aspect. Furthermore, no fair combination of any of these references with each other or with the prior art needle electrode disclosed herein or with the prior art method disclosed herein appears to render the present invention obvious.

The manner in which the present invention attains the foregoing objects and advantages will appear more clearly hereafter.

SUMMARY OF THE INVENTION

A needle electrode embodying the invention comprises a ferrule that is symmetrical about an axis and with a distal end and a proximal end, the ferrule having a nose portion at the distal end and defining in turn from the distal end a nose passage terminating at a shoulder communicating with a proximal opening conical guide passage having a proximal guide opening, followed by an outwardly splayed abutment opening into an annular recess.

The electrode of the invention further comprises a cannula with a distal end and a proximal end which penetrates into the nose passage and abuts the shoulder. The nose portion is connected about the proximal end of the cannula.

The electrode of the invention further has an insulator spool having a distal end and an axial bore smaller than the guide opening and aligned axially therewith.

Additionally, the electrode of the invention has a wire with a proximal end and a distal end, and a connector member with a cavity for receiving the proximal end of the wire therein. The connector member is attached about the cavity onto the proximal end of the wire, and the connector member is mounted into the axial bore of the insulator spool and secured therein.

The insulator spool is in the annular recess with the distal end of the wire penetrating in turn through the axial bore, then through the guide opening, and then through an interior passage in the cannula until the distal end of the insulator spool engages the abutment.

A method embodying the invention for assembling a needle electrode comprises the steps of providing a ferrule, a cannula, an insulator spool, a wire, and a connector member as described above, connecting the nose portion of the ferrule about the proximal end of the cannula, attaching the connector member about the cavity onto the proximal end of the wire, mounting the connector member into the axial bore of the insulator spool and securing it therein, and inserting the insulator spool into the annular recess with the distal end of the wire penetrating in turn the axial bore, the guide opening and into an interior passage in the cannula until the distal end of the insulator spool engages the abutment.

DESCRIPTION OF THE INVENTION

Figure 1A:
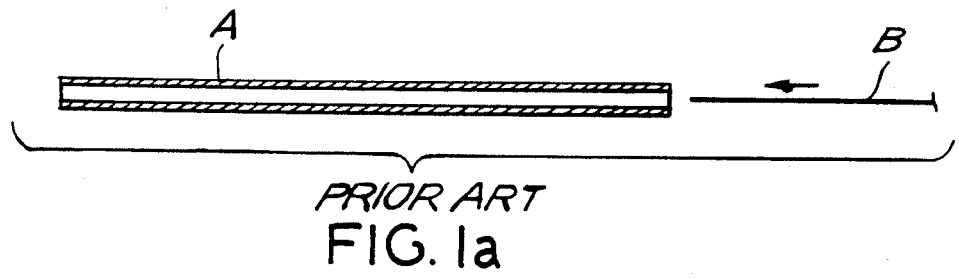
FIGS. 1a, 1b and 1c depict the prior art method of assembling a needle electrode and the prior art needle electrode.
Figure 1B:
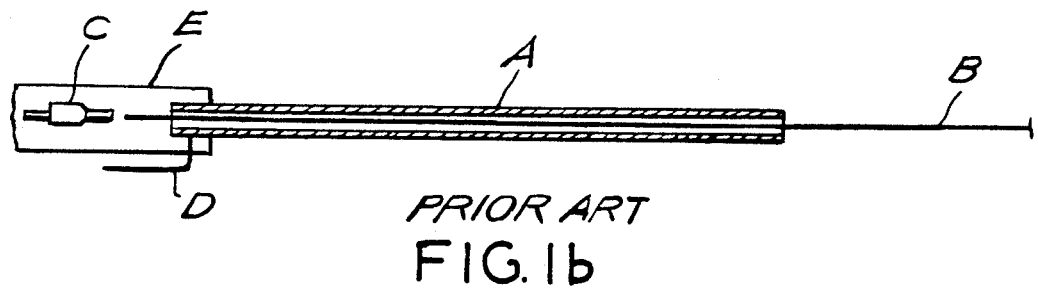
Figure 1C:
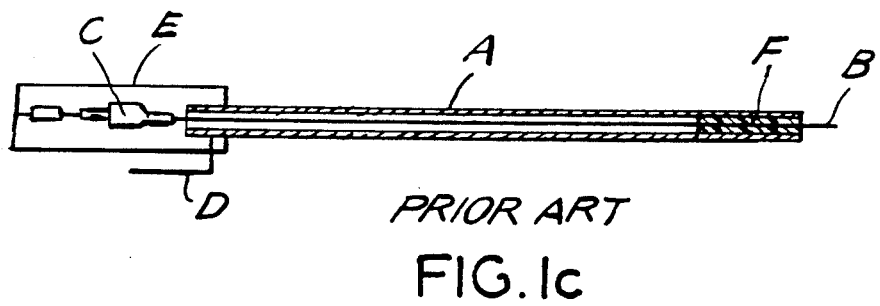

FIGS. 1a, 1b and 1c depict the prior art method of assembling a commonly-used prior art needle electrode. FIG. 1a shows a cannula A and a needle wire B. As shown by the arrow, needle wire B is about to enter the right-hand end of cannula A. Needle wire B is pushed through cannula A until needle wire B emerges from the end of cannula A. A sufficient length of needle wire B is pushed through cannula A so that an electrode connector or pin C may be fastened to needle wire B as shown in FIG. 1b. A wire D is then connected to cannula A to assist in holding the assembly while cannula A, needle wire B, connector C and an insulating ferrule E are secured in position as shown in FIG. 1c by a suitable known means. This part of the assembly is then completed by the insertion of a potting compound F into the right-hand end or front only of cannula A as also shown in FIG. 1c. Needle wire B is then trimmed to length and ground by known means to the desired shape. The assembly of cannula A, needle wire B and connector C is then ready to be provided with a handle member, electrical connections and an outer protective sheath to form a disposable needle electrode.

The difficulties of the prior art method as described in the preceding paragraph and the shortcomings of the prior art needle electrode produced by the prior art method are as set forth above. To summarize those difficulties and shortcomings, it is arduous and time-consuming and expensive to thread needle wire B through cannula A and such threading can result in short-circuiting the needle electrode and rendering same unfit for use.

Figure 2:
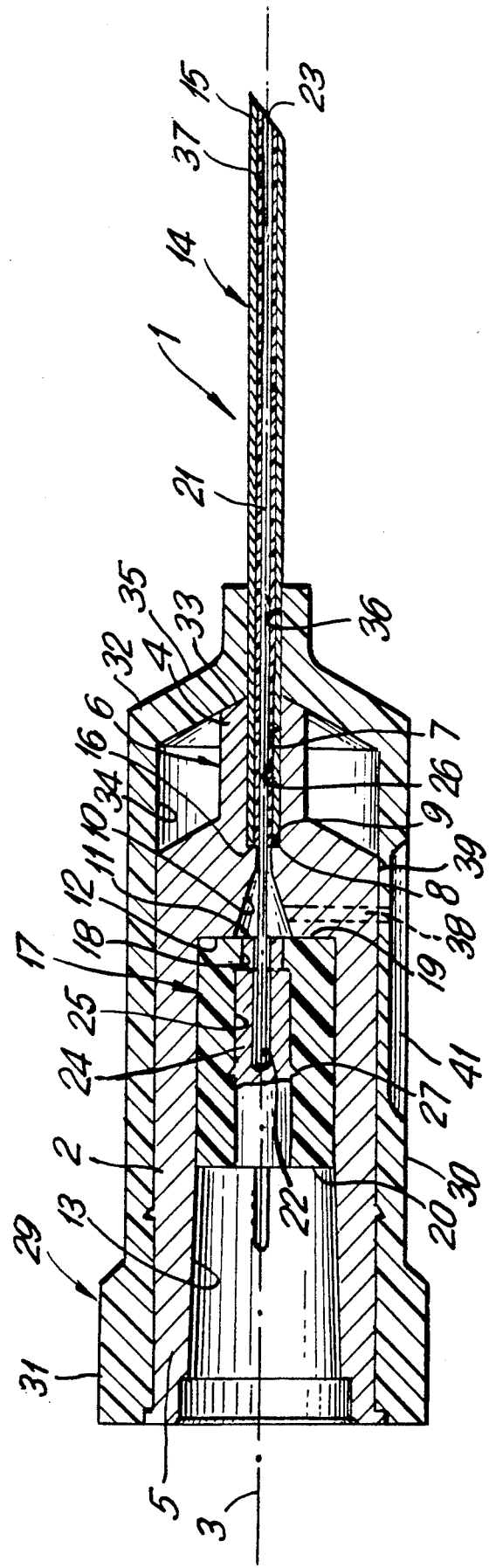
FIG. 2 is an axial sectional view depicting a disposable needle electrode that is a preferred embodiment of the invention and also furnishing a basis for understanding the method of the invention.

FIG. 2 shows a needle electrode 1 that is a preferred embodiment of the invention. Electrode 1 comprises a ferrule 2 of conductive material, for example, brass, symmetrical about an axis 3 and having a distal end 4 and a proximal end 5. Ferrule 2 has a nose portion 6 at distal end 4 and defining in turn from distal end 4 a nose passage 7 terminating at an end 8 with a shoulder 9 communicating with a proximally opening conical guide passage 10 having a proximal guide opening 11, followed by an outwardly splayed abutment 12 to open into an annular recess 13.

Electrode 1 further includes a cannula 14 having a distal end 15 and a proximal end 16, which penetrates into nose passage 7 and abuts shoulder 9.

Nose portion 6 is connected about proximal end 16 of cannula 14.

Electrode 1 also comprises an insulator spool 17 with an axial bore 18 that is smaller than guide opening 11 and aligned axially therewith, spool 17 being provided with a distal end 19 and a proximal end 20.

A wire 21 is another component of electrode 1 and has a proximal end 22 and a distal end 23, and a connector member 24 with a cavity 25 is adapted to receive proximal end 22 of wire 21 thereon. Connector member 24 is attached about cavity 25 onto proximal end 22 of wire end 21, and connector member 24 is mounted into axial bore 18 of spool 17 and is secured therein.

Spool 17 is positioned in annular recess 13 with distal end 23 of wire 21 penetrating in turn through axial bore 18, then through guide opening 11, and then through an interior passage 26 formed in cannula 14 until distal end 19 of spool 17 engages abutment 12.

Nose portion 6 of ferrule 2 is crimped about proximal end of cannula 14, and connector member 24 is crimped about cavity 25 onto proximal end 22 of wire 21. An annular lip 27 is formed outward on connector member 24, and insulation spool 17 is made of plastic that is soft enough to lock lip 27 in spool 17.

Needle electrode 1 further includes a handle member 29 having a proximal end 31 and a distal end 32. Nose portion 6 of ferrule 2 is cylindrical and terminates at its distal end 4 in a cone 33. An interior wall 34 of distal end 32 of handle member 29 is formed as a cylinder and has a conical portion 35 to nest axially nose portion 6 telescopically therein. Distal end 32 of handle member 29 is also furnished with an axial bore 36 for passage of cannula 14 therethrough.

Needle electrode 1 is furnished with insulating material 37 between wire 21 and cannula 14 and has a vent hole 38 extending between guide passage 11 and the outside 39 of ferrule 2 so as to facilitate placing of insulating material 37. Distal end 15 of cannula 14 in ferrule 2 is ground and sharpened with wire 21 to a beveled surface at distal end 23. Insulating material 37 is imbibed between needle wire 21 and cannula 14 and proceeds towards vent hole 38 by capillary action.

Needle electrode 1 is also provided with means for connecting cannula 14 to an electrical terminal via ferrule 2, and handle member 29 defines an elongated scallop 41 on a handle surface 30 to indicate orientation with the beveled surface at distal end 23.

As stated, the invention also contemplates a method of assembling needle electrode 1. The method, which will be described with reference to FIG. 2, comprises the steps of providing ferrule 2, cannula 14, insulator spool 17, wire 21 and connector member 24 as described above. The method includes the further steps of attaching connector member 24 with cavity 25 adapted to receive proximal end 22 of wire 21 therein, mounting connector member 24 into axial bore 18 of insulator spool 17 and securing it therein, and inserting spool 17 into the annular recess 13 with distal end 23 of wire 21 penetrating in turn through axial bore 18, then through guide opening 11 thereby facilitating a concentric assembly, then into interior passage 26 formed in cannula 14 until distal end 19 of insulator spool 17 engages abutment 12.

The assembly method further includes, to achieve the connection of nose portion 6 about proximal end 16 of cannula 14, crimping nose portion 6 thereon, and to achieve the attachment of connector 24 about cavity 25 onto proximal end 22 of wire 21, crimping connector member 24 thereon.

The assembly method also includes the steps of providing annular lip 27 outward on connector member 24, and providing insulator spool 17 of plastic soft enough to lock lip 27 thereon.

The assembly method further includes, to achieve the connection of nose portion 6 about proximal end 16 of cannula 14, crimping nose portion 6 thereon, and to achieve the attachment of connector member 24 about cavity 25 onto proximal end 22 of wire 21, crimping connector member 24 thereon.

The assembly method further includes the steps of providing handle member 29 having proximal end 31 and distal end 32, forming nose portion 6 of ferrule 2 cylindrical and terminating it at its distal end 4 in cone 33, forming an interior wall 34 of distal end 32 of handle member 29 as a cylinder and having cylindrical portion 35 to nest axially nose portion 6 telescopically therein thereby facilitating a concentric assembly, and furnishing distal end 32 of handle member 29 with axial bore 36 for passage of cannula 14 therethrough.

The method also includes the steps of placing insulating material 37 between wire 21 and cannula 14, providing vent hole 38 extending between guide passage 11 and outside 39 of ferrule 2 so as to facilitate placing of the insulating material 37, grinding and shaping distal end 15 of cannula 14 mounted in the ferrule 2 with wire 21 and insulating material 37 installed, connecting cannula 14 to an electrical terminal via ferrule 2 thereby providing a concentric electrical connection, and providing handle member 29 with elongated scallop 41 to indicate orientation with the beveled surface at distal end 23.

It is apparent that the invention in both its article aspect and its method aspect well attains the stated objects and advantages, among others.

Disclosed details are exemplary only and are not to be taken as limitations on the invention except as the details may be included in the appended claims.

What is claimed is:

1. A needle electrode (1) comprising in combination:
a ferrule (2) having a distal end (4) and a proximal end (5), the ferrule (2) provided with a nose portion (6) at the distal end (4) thereof and defining in turn from the distal end (4) a nose passage (7) terminating in a shoulder (9), the nose passage (7) communicating with a proximally opening conical guide passage (10) ending in a proximal guide opening (11), the proximal guide opening (11) defining an abutment surface (12) bounded by an annular recess (13) in the ferrule (2);
an insulator spool (17) located within the annular recess (13) of the ferrule (2) and including an axial bore (18) smaller than the guide opening (11) and aligned axially therewith;
a cannula (14) in the nose passage (7) and abutting the shoulder (9) and extending distally from the nose passage (7); and
wherein a needle wire (21) with a cooperating connector member (24) attached thereto is inserted in the cannula (14) via the axial bore (18) and then the conical guide passage (10) whereby the needle wire (21) extends from within the insulator spool (17) through the cannula (14).

2. The needle electrode (1) as set forth in claim 4, with insulating material (37) between the wire (21) and the cannula (14).

3. The needle electrode (1) as set forth in claim 2, with the ferrule (2) having an outside (39), a vent hole (38) extending between the guide opening (11) and the outside (39) so as to facilitate placing of the insulating material (37).

4. A needle electrode (1) comprising in combination:
a ferrule (2) symmetrical about an axis (3) and having a distal end (4) and a proximal end (5), the ferrule (2) provided with a nose portion (6) at the distal end (4) thereof and defining in turn from the distal end (4) a nose passage (7) terminating at a shoulder (9) communicating with a proximally opening conical guide passage (10) having a proximal guide opening (11) followed by an outwardly splayed abutment (12) to open into an annular recess (13);
a cannula (14) having a distal end (15) and a proximal end (16), the proximal end (16) of the cannula (14) penetrating into the nose passage (7) and abutting the shoulder (9);
the nose portion (6) connected about the proximal end (16) of the cannula (14);
an insulator spool (17) with an axial bore (18) smaller than the guide opening (11) and aligned axially therewith, the spool (17) having a distal end (19);
a wire (21) having a proximal end (22) and a distal end (23);
a connector member (24) provided with a cavity (25) adapted to receive the proximal end (22) of the wire (21) therein;
the connector member (24) attached about the cavity (25) onto the proximal end (22) of the wire (21);
the connector member (24) mounted into the axial bore (18) of the insulator spool (17) and secured therein; and
the insulator spool (17) positioned in the annular recess (13) with the distal end (23) of the wire (21) penetrating in turn through the axial bore (18), then through the guide opening (11), and then through an interior passage (26) formed in the cannula (14) with the distal end (19) of the insulator spool (17) abutting the abutment (12).

5. The needle electrode (1) as set forth in claim 4, with the nose portion (6) crimped about the proximal end (16) of the cannula (14).

6. The needle electrode (1) as set forth in claim 5, with the connector member (24) crimped about the cavity (25) onto the proximal end (22) of the wire (21).

7. The needle electrode (1) as set forth in claim 6, with:
an annular lip (27) formed outward on the connector member (24), and
the insulator spool (17) made of plastic soft enough to lock the lip (27) therein.

8. The needle electrode (1) as set forth in claim 4, with:
a handle member (29) having a proximal end (31) and a distal end (32),
the nose portion (6) of the ferrule (2) being cylindrical and terminating at its distal end (4) in a cone (33),
an interior wall (34) of the distal end (32) of the handle member (29) formed as a cylinder and having a conical portion (35) to nest axially the nose portion (6) telescopically therein, and
the distal end (32) of the handle member (29) also furnished with an axial bore (36) for passage of the cannula (14) therethrough.

9. The needle electrode (1) as set forth in claim 8 with the handle member (29) defining an elongated scallop (41) on an outside surface of the handle member (29) to indicate orientation.

10. The needle electrode (1) as set forth in claim 4, with the distal end (15) of the cannula (14) ground and sharpened with the wire (21) and the insulating material (37) installed.

11. The needle electrode (1) as set forth in claim 4 with means for connecting the cannula (14) to an electrical terminal via the ferrule (2).

12. A method for assembling a needle electrode (1) and comprising steps as follows:
   a ferrule (2) symmetrical about an axis (3) and having a distal end (4) and a proximal end (5), the ferrule (2) provided with a nose portion (6) at its distal end (4) and defining in turn from the distal end (4) a nose passage (7) terminating at a shoulder (9) communicating with a proximally opening conical guide passage (10) having a proximal guide opening (11) followed by an outwardly splayed abutment (12) to open into an annular recess (13);
   providing a cannula (14) having a distal end (15) and a proximal end (16) and inserting the proximal end (16) of the cannula into the nose passage (7) until it abuts the shoulder (9);
   connecting the nose portion (6) about the proximal end (16) of the cannula;
   providing an insulator spool (17) with an axial bore (18) smaller than the guide opening (11) and aligned axially therewith, the insulator spool (17) having a distal end (19);
   providing a wire (21) with a proximal end (22) and a distal end (23);
   providing a connector member (24) with a cavity (25) adapted to receive the proximal end (22) of the wire (21) therein;
   attaching the connector member (24) about the cavity (25) onto the proximal end (22) of the wire (21);
   mounting the connecting member (24) into the axial bore (18) of the insulator spool (17) and securing it therein;
   inserting the insulator spool (17) into the annular recess (13) with the distal end (19) of the spool (17) against the splayed abutment (12) of the ferrule (2); and
   inserting the connector member (24) into the axial bore (18) with the distal end (23) of the wire (21) penetrating in turn through the axial bore (18), then through the guide opening (11) and then into an interior passage (26) formed in the cannula (14) until the distal end (19) of the insulator spool (17) engages the abutment (12).

13. The method of claim 12 and, to achieve said connecting of the nose portion (6) about the proximal end (16) of the cannula (14), crimping the nose portion (6) thereon.

14. The method of claim 12 and, to achieve attaching of the connector member (24) about the cavity (25) onto the proximal end (22) of the wire (21), crimping the connector member (24) thereon.

15. The method of claim 14 and:
   providing an annular lip (27) formed outward on the connector member (24), providing the insulator spool (17) of plastic soft enough to lock the lip (27) therein.

16. The method of claim 12 and:
   providing a handle member (29) having a proximal end (31) and a distal end (32);
   forming the nose portion (6) of the ferrule (2) cylindrical and terminating at its distal end (4) in a cone (33);
   forming an interior wall (34) of the distal end (32) of the handle member (29) as a cylinder and having a cylindrical portion (35) to nest axially the nose portion (6) telescopically therein;
   furnishing the distal end (32) of the handle member (29) with an axial bore (36) for passage of the cannula (14) therethrough; and
   mounting the ferrule (2) about the cannula (14) and mounting the handle member (29) about the cannula (14) and the ferrule (2).

17. The method of claim 16 and providing the handle member (29) with an elongated scallop (41) on an outside surface of the handle to indicate orientation.

18. The method of claim 12 and placing insulating material (37) between the wire (21) and the cannula (14).

19. The method of claim 18 and the ferrule (2) having an outer side (39), providing a vent hole (38) extending between the guide opening (11) and the outer side (39) so as to facilitate placing of the insulating material (37) via the vent hole (38).

20. The method of claim 18 and grinding and sharpening the distal end (15) of the cannula (14) with the wire (21) and the insulating material (37) installed.

21. The method of claim 12 and connecting the cannula to an electrical terminal via the ferrule (2).

* * * * *